(12) United States Patent
Dorian et al.

(10) Patent No.: US 7,901,584 B2
(45) Date of Patent: Mar. 8, 2011

(54) PLASMA CONCENTRATION

(75) Inventors: Randel Dorian, San Diego, CA (US); Michael D. Leach, Warsaw, IN (US); Richard W. Storrs, Berkeley, CA (US)

(73) Assignees: Hanuman, LLC, San Francisco, CA (US); Biomet Biologics, Warsaw, IN (US)

( * ) Notice: Subject to any disclaimer, the term of this patent is extended or adjusted under 35 U.S.C. 154(b) by 59 days.

(21) Appl. No.: 12/476,838

(22) Filed: Jun. 2, 2009

(65) Prior Publication Data
US 2009/0236297 A1    Sep. 24, 2009

Related U.S. Application Data

(62) Division of application No. 11/342,982, filed on Jan. 30, 2006, now Pat. No. 7,553,413.

(60) Provisional application No. 60/650,860, filed on Feb. 7, 2005.

(51) Int. Cl.
*B01D 15/02* (2006.01)
*B01D 33/27* (2006.01)
*B01D 37/00* (2006.01)

(52) U.S. Cl. ......... 210/782; 210/806; 210/219; 210/297; 210/502.1; 422/44; 422/72; 436/177; 436/178

(58) Field of Classification Search .......... 210/782, 210/806, 219, 297, 502.1; 422/44, 72, 102; 436/177, 178
See application file for complete search history.

(56) References Cited

U.S. PATENT DOCUMENTS

| | | |
|---|---|---|
| 3,723,244 A | 3/1973 | Breillatt, Jr. |
| 3,850,369 A | 11/1974 | Bull et al. |
| 3,897,343 A | 7/1975 | Ayres |
| 3,909,419 A | 9/1975 | Ayres |
| 3,931,010 A | 1/1976 | Ayres et al. |
| 3,931,018 A | 1/1976 | North, Jr. |
| 3,982,691 A | 9/1976 | Schlutz |
| 4,046,699 A | 9/1977 | Zine, Jr. |
| 4,055,501 A | 10/1977 | Cornell |
| 4,077,396 A | 3/1978 | Wardlaw et al. |
| 4,154,690 A | 5/1979 | Ballies |
| 4,187,979 A | 2/1980 | Cullis et al. |
| 4,322,298 A | 3/1982 | Persidsky |
| 4,379,849 A | 4/1983 | Heimreid |

(Continued)

FOREIGN PATENT DOCUMENTS

EP    0244834 A2    11/1987

(Continued)

OTHER PUBLICATIONS

Fibrostik™ Plasma Concentrator, Attention Operating Surgeon, Cell Factor Technologies, Inc., Jul. 2003.

(Continued)

*Primary Examiner* — David A Reifsnyder
(74) *Attorney, Agent, or Firm* — Harness, Dickey (57) ABSTRACT

A plasma concentrator having a concentrator chamber, concentrator gel beads, a filter, and an agitator. The agitator end is positioned in the concentrator chamber and supported for rotation about its central axis and for reciprocal movement along its central axis. A filter is selected to block effective flow of plasma therethrough under ambient gravity conditions and permit plasma and plasma concentrate flow therethrough under centrifugal forces of the separation gravity. A method concentrates plasma by removing water without significantly denaturing the fibrinogen in the plasma. Then centrifugal force can be applied to the concentrated plasma in an amount sufficient to separate a substantial portion of the plasma concentrate from the beads.

24 Claims, 4 Drawing Sheets

U.S. PATENT DOCUMENTS

| | | |
|---|---|---|
| 4,416,654 A | 11/1983 | Schoendorfer et al. |
| 4,464,167 A | 8/1984 | Schoendorfer et al. |
| 4,675,117 A | 6/1987 | Neumann et al. |
| 4,714,457 A | 12/1987 | Alterbaum |
| 4,776,964 A | 10/1988 | Schoendorfer et al. |
| 4,818,386 A | 4/1989 | Burns |
| 5,019,243 A | 5/1991 | McEwen et al. |
| 5,053,127 A | 10/1991 | Schoendorfer et al. |
| 5,131,907 A | 7/1992 | Williams et al. |
| 5,141,645 A | 8/1992 | Shiraki et al. |
| 5,147,290 A | 9/1992 | Jonsson et al. |
| 5,165,938 A | 11/1992 | Knighton |
| 5,171,456 A | 12/1992 | Hwang et al. |
| 5,185,001 A | 2/1993 | Galanakis |
| 5,234,608 A | 8/1993 | Duff |
| 5,269,927 A | 12/1993 | Fiehler |
| 5,271,852 A | 12/1993 | Luoma, II |
| 5,318,782 A | 6/1994 | Weis-Fogh et al. |
| 5,322,620 A | 6/1994 | Brown et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |
| 5,403,272 A | 4/1995 | Deniega et al. |
| 5,456,885 A | 10/1995 | Coleman et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,549,683 A | 8/1996 | Bonutti |
| 5,560,830 A | 10/1996 | Coleman et al. |
| 5,585,007 A | 12/1996 | Antanavich et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,895 A | 5/1997 | Tsukagoshi et al. |
| 5,632,905 A | 5/1997 | Haynes |
| 5,649,903 A | 7/1997 | Deniega et al. |
| 5,707,331 A | 1/1998 | Wells et al. |
| 5,707,876 A | 1/1998 | Levine |
| 5,733,466 A | 3/1998 | Benebo et al. |
| 5,733,545 A | 3/1998 | Hood, III |
| 5,788,662 A | 8/1998 | Antanavich et al. |
| 5,795,571 A | 8/1998 | Cederholm-Williams et al. |
| 5,795,751 A | 8/1998 | Apel |
| 5,817,519 A | 10/1998 | Zelmanovic et al. |
| 5,833,866 A | 11/1998 | Brown |
| 5,834,418 A | 11/1998 | Brazeau et al. |
| 5,837,150 A | 11/1998 | Langley et al. |
| 5,863,892 A | 1/1999 | Stern et al. |
| 5,865,785 A | 2/1999 | Bischof |
| 5,899,874 A | 5/1999 | Jonsson et al. |
| 5,900,245 A | 5/1999 | Sawhney et al. |
| 5,934,803 A | 8/1999 | Hutter |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm |
| 5,980,734 A | 11/1999 | Itoh et al. |
| 6,010,627 A | 1/2000 | Hood, III |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,274,090 B1 | 8/2001 | Coelho et al. |
| 6,280,400 B1 | 8/2001 | Niermann |
| 6,296,602 B1 | 10/2001 | Headley |
| 6,368,298 B1 | 4/2002 | Beretta et al. |
| 6,417,004 B1 | 7/2002 | Brady et al. |
| 6,444,228 B1 | 9/2002 | Baugh et al. |
| 6,472,162 B1 | 10/2002 | Coelho et al. |
| 6,516,953 B1 | 2/2003 | DiCesare et al. |
| 6,596,180 B2 | 7/2003 | Baugh et al. |
| 6,719,901 B2 | 4/2004 | Dolecek et al. |
| 6,733,471 B1 | 5/2004 | Ericson et al. |
| 6,905,612 B2 | 6/2005 | Dorian et al. |
| 7,179,391 B2 | 2/2007 | Leach et al. |
| 2002/0090711 A1 | 7/2002 | Karlsson |
| 2002/0114775 A1 | 8/2002 | Pathak |
| 2002/0169408 A1 | 11/2002 | Beretta et al. |
| 2002/0172666 A1 | 11/2002 | Sacchi et al. |
| 2003/0198687 A1 | 10/2003 | Bennett et al. |
| 2004/0120942 A1 | 6/2004 | McGinnis et al. |
| 2004/0182795 A1 | 9/2004 | Dorian et al. |
| 2005/0109716 A1 | 5/2005 | Leach et al. |
| 2006/0009855 A1 | 1/2006 | Goble et al. |
| 2006/0243676 A1 | 11/2006 | Swift et al. |

FOREIGN PATENT DOCUMENTS

| | | |
|---|---|---|
| EP | 1079224 A2 | 2/2001 |
| WO | WO-9812274 A1 | 3/1998 |
| WO | WO-9967277 A1 | 12/1999 |
| WO | WO-0238610 A1 | 5/2002 |
| WO | WO-02060925 A1 | 8/2002 |
| WO | WO-03099412 A1 | 12/2003 |
| WO | WO-2004009207 A1 | 1/2004 |

OTHER PUBLICATIONS

International Search Report for PCT/US2006/003598 mailed Jan. 6, 2006 claiming benefit of U.S. Appl. No. 60/640,860, filed Feb. 7, 2005.

PLASMA CONCENTRATION

CROSS-REFERENCE TO RELATED APPLICATIONS

This application is a divisional of U.S. patent application Ser. No. 11/342,982 filed on Jan. 30, 2006, now U.S. Pat. No. 7,553,413 issued on Jun. 30, 2009, which claims the benefit under 35 USC 120 of the filing date of U.S. Provisional Application No. 60/650,860 filed Feb. 7, 2005. The entire disclosures of the above applications are incorporated herein by reference.

FIELD

This invention relates to an apparatus and method for preparing a plasma concentrate that can be used as a tissue sealant and a hemostat. Then plasma concentrate is preferably free of cells.

BACKGROUND

This section provides background information related to the present disclosure which is not necessarily prior art.

Blood can be fractionated, and the different fractions of the blood can be used for different medical needs. Under the influence of gravity or centrifugal force, blood spontaneously sediments into three layers. At equilibrium, the top low-density layer is a straw-colored clear fluid called plasma. Plasma is a water solution of salts, metabolites, peptides, and many proteins ranging from small (insulin) to very large (complement components).

The bottom, high-density layer is a deep red viscous fluid comprising anuclear red blood cells (erythrocytes) specialized for oxygen transport. The red color is imparted by a high concentration of chelated iron or heme that is responsible for the erythrocytes' high specific gravity. The relative volume of whole blood that consists of erythrocytes is called the hematocrit, and in normal human beings this can range from about 37% to about 52% of whole blood.

The intermediate layer is the smallest, appearing as a thin white band above the erythrocyte layer and below the plasma layer; this is called the buffy coat. The buffy coat itself has two major components, nucleated leukocytes (white blood cells) and anuclear smaller bodies called platelets (or thrombocytes). Leukocytes confer immunity and contribute to debris scavenging. Platelets seal ruptures in blood vessels to stop bleeding, and deliver growth and wound healing factors to a wound site. Slower speed or shorter duration centrifugation permits separation of erythrocytes and leucocytes from plasma, while the smaller platelets remain suspended in the plasma, yielding platelet rich plasma (PRP).

A major improvement in making plasma concentrate from whole blood for use in wound healing and as a tissue sealant was described in U.S. Pat. No. 5,585,007; this patent is hereby incorporated by reference in its entirety. This device, designed for placement in a medical laboratory or surgical amphitheater, with an integral centrifuge used a disposable cartridge for preparing tissue sealant. The device was particularly applicable for stat preparations of autologous tissue sealants. Preparation in the operating room of 5 ml of sealant from 50 ml of patient blood required less than 15 minutes and only one simple operator step. There was no risk of tracking error because processing can be done in the operating room. Chemicals added could be limited to anticoagulant (e.g., citrate) and calcium chloride. The disposable cartridge could fit in the palm of the hand and was hermetically sealed to eliminate possible exposure to patient blood and ensure sterility. Adhesive and tensile strengths of the product were comparable or superior to pooled blood fibrin sealants made with precipitation methods. Use of antifibrinolytic agents (such as aprotinin) was not necessary because the tissue sealant contained high concentrations of natural inhibitors of fibrinolysis from the patient's blood. This new tissue sealant also optionally contained patient platelets and additional factors that promote wound healing, healing factors that are not present in commercially available fibrin sealants.

The patented device used a new sterile disposable cartridge with the separation chambers for each run. Since the device was designed to be used in a normal medical setting with ample power, the permanent components, designed for long-term durability, safety, and reliability, were relatively heavy, using conventional centrifuge motors and accessories.

Disposable plasma concentrating devices suitable for concentrating PRP according to this invention are described in commonly assigned, application Ser. No. 10/394,828 filed Mar. 21, 2003, now U.S. Pat. No. 6,905,612 issued on Jun. 14, 2005, the entire contents of which are hereby incorporated by reference. The cell-free plasma fraction is removed and discarded.

SUMMARY

This section provides a general summary of the disclosure, and is not a comprehensive disclosure of its full scope or all of its features.

The disposable device of this invention is suitable for preparing a highly valuable autologous plasma concentrate from cell-free plasma fractions.

The concentrating phase requires only simple manual manipulation (rotating the agitator shaft with reciprocal movement to disrupt gel bead clumping). The device is then spun with a conventional centrifuge to separate the plasma concentrate from the desiccated beads, moving the plasma concentrate from the concentrating zone into a plasma concentrate reservoir, from which it can be removed by a conventional applicator syringe.

The plasma concentrator of this invention comprises a concentrator chamber, a plurality of concentrator gel beads in the concentrator chamber, a filter, and an agitator. The agitator comprises an actuator stem having an upper agitator end and a lower agitator end, agitator blades extending outwardly from the lower end. The lower agitator end is positioned in the concentrator chamber, and mounted or supported for both rotation about its central axis and for reciprocal movement along its central axis. The concentrator has a top with an upper opening through which the upper end of the actuator stem extends, and a lower opening in which the filter is positioned. The concentrator chamber can have a cylindrical inner wall, and the agitator blades can have an outer edge in close proximity to the inner wall with the space between the outer edge and the inner wall being less than the diameter of the gel beads.

The upper opening of the concentrator can include a stop sleeve extending from the top of the concentrator into the concentrator chamber, the stop sleeve having a lower abutment surface. The agitator stem can have stop projections that extend outward beyond the diameter of the strop sleeve, the upper surfaces of the stop projections constituting abutment surfaces positioned to stop upward axial movement of the agitator when contacting the lower abutment surface of the stop sleeve.

The filter has an upper surface and the agitator blades can have a lower portion that contacts the upper surface of the filter and is positioned for sweeping the upper surface during rotation of the agitator and for making impact with the upper surface during downward movement of the agitator along its central axis. The downward motion of the blades during the reciprocal movement of the agitator can be arrested by abutment with the upper surface of the filter.

The filter is selected to block effective flow of plasma therethrough under ambient gravity conditions and permits plasma concentrate flow therethrough under centrifugal forces above 10 g's and up to at least as high as the separation gravity.

The plasma concentrator can be combined with a plasma concentrate outlet conduit and a plasma concentrate reservoir with an upper opening in communication with the filter and positioned to receive plasma concentrate passing through the filter. The plasma concentrator can have a sloping floor and a sump at the lowest end of the floor, one end of the plasma concentrate outlet conduit communicating with the sump.

The method of this invention for concentrating plasma by removing water without significantly denaturing the fibrinogen in the plasma can include introducing the plasma into a concentration chamber containing a plurality of dehydrated concentrator gel beads and an agitator. Then water is removed from the plasma until the plasma has a protein concentration greater than 1.5 times the protein concentration of the untreated plasma.

While the water is being removed, the agitator can be rotated to stir the beads to reduce plasma polarization and moved to break up clumps of beads that form during the agitation. Then centrifugal force can be applied to the concentrated plasma in an amount sufficient to separate a substantial portion of the plasma concentrate from the beads.

When the concentration chamber contains an agitator having agitator blades extending outwardly from its lower end, wherein the agitator is supported for rotation about its central axis and for reciprocal movement along its central axis, the agitator can be rotated to stir the beads while they are absorbing water from the plasma to reduce plasma polarization, and the agitator can be moved along its central axis in a reciprocal motion to break up clumps of beads that form during the agitation.

If the agitator blades rest on the upper surface of a filter, the agitator blades can have a lower portion that sweeps the upper surface of the filter during rotation, and impacts the upper surface of the filter during reciprocal motion of the agitator along its central axis. Then the agitator can be rotated to sweep the upper surface of the filter and stirring beads resting thereupon to reduce plasma polarization, and the agitator can be moved in a reciprocal motion to impact the upper surface of the filter and bead clumps forming on the surface during the stirring.

When the filter has pores that block effective flow of plasma therethrough under ambient gravity conditions and permits plasma and plasma concentrate therethrough at more than 10 g's and up to the separation gravity. The plasma can be maintained in contact with the beads by the filter during the water removal and plasma concentrate can be caused to flow through the filter when the mixture is subjected to centrifugal forces in the direction of the filter of as high as the separation gravity.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

The term "separation gravity" is a centrifugal force that is sufficient to separate plasma concentrate from the surface of the concentrator gel beads and to cause separated plasma concentrate to flow through the filter.

The device is one component of an improvement over the complex plasma separating and concentrating device described in U.S. Pat. No. 5,585,007. A disposable device described in application Ser. No. 10/394,828 filed Mar. 21, 2003, rapidly separates plasma from blood using a conventional medical laboratory centrifuge. The device of this invention converts the plasma into an autologous concentrate highly useful as a tissue sealant and hemostat.

Figure 1:
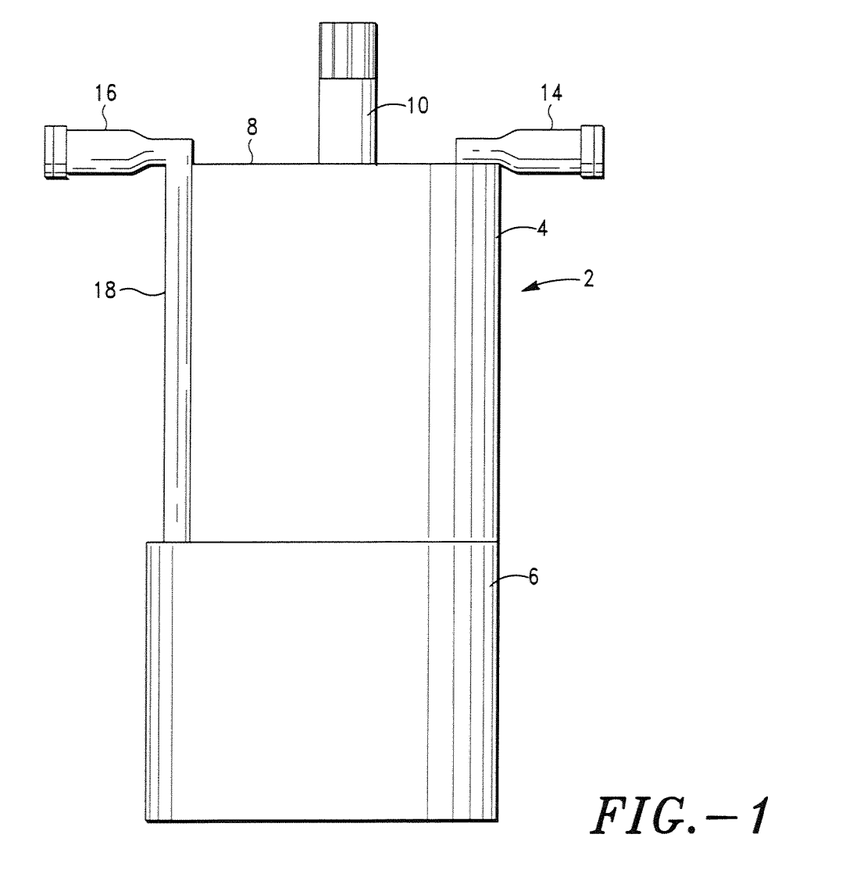
FIG. 1 is a front view of the plasma concentrating device of this invention.
Figure 2:
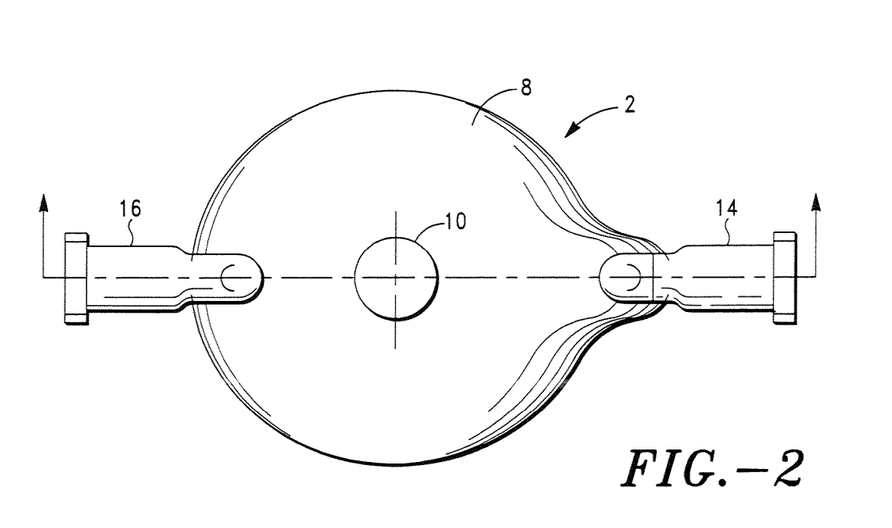
FIG. 2 is a top view of the plasma concentrating device shown in FIG. 1.

Referring to the drawings, FIG. 1 is a front view of the plasma concentrating device of this invention, and FIG. 2 is a top view of the plasma concentrating device shown in FIG. 1. This small compact device is suitable for processing up to 50 ml of plasma. The concentrator 2 has an upper concentrator housing 4 and a lower concentrate reservoir housing 6. The upper concentrator housing 4 has a top 8 through which the agitator stem 10 of a gel bead agitator 12 (See FIGS. 3-5) extends. The top 8 also has a plasma inlet port 14 that extends through the top 8 and communicates with the concentration chamber 20 (FIG. 3) enclosed by the upper concentrating housing 4. A plasma concentrate outlet port 16 communicates with a plasma concentrate conduit 18 shown in greater detail in FIG. 3.

Figures 3, 4:
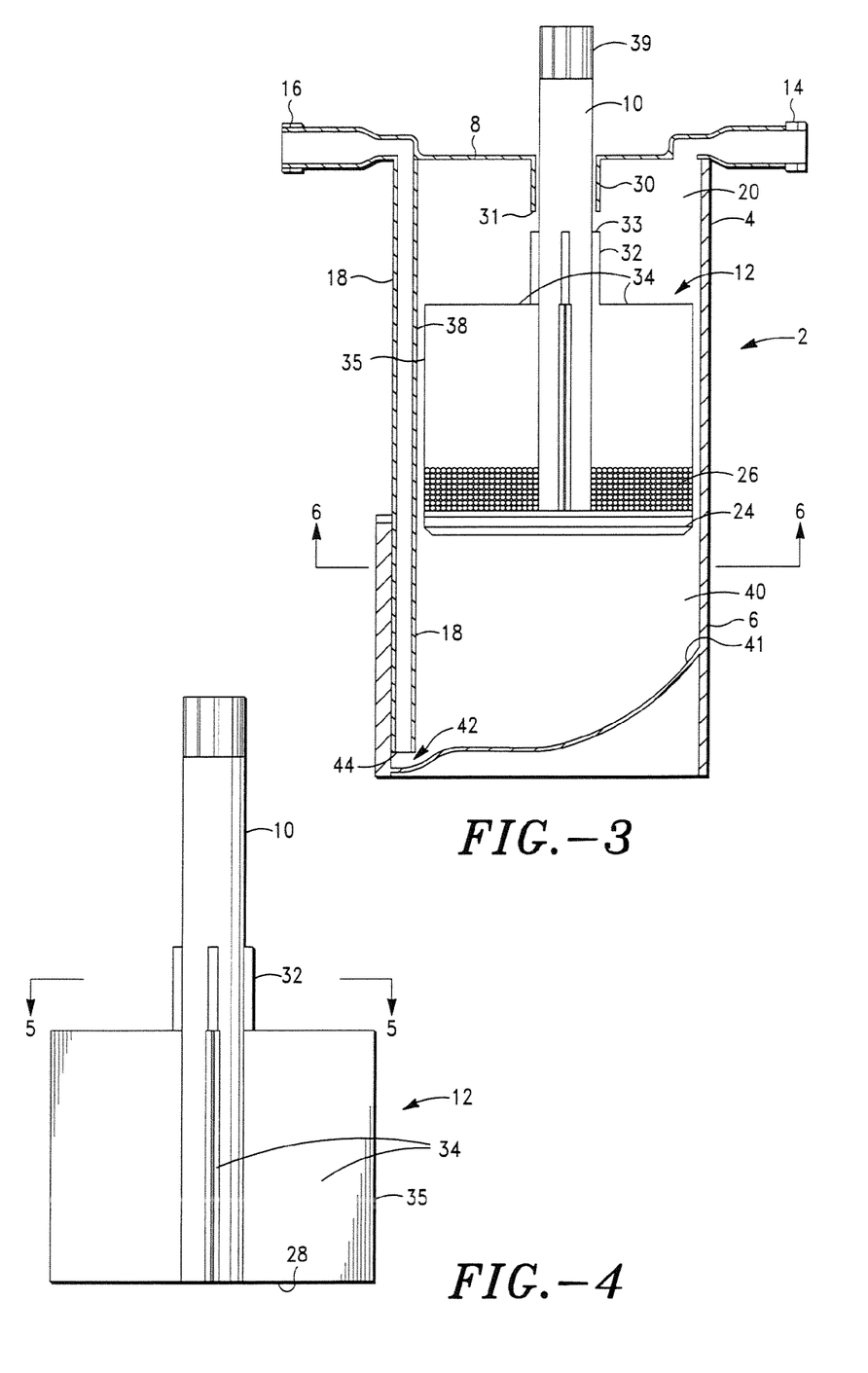
FIG. 3 is a cross-sectional drawing of the plasma concentrating device shown in FIG. 1 taken along the line 3-3 of FIG. 2.
FIG. 4 is a front view of the agitator component of the plasma concentrating device of this invention.

FIG. 3 is a cross-sectional drawing of the plasma concentrating device shown in FIG. 1 taken along the line 3-3 of FIG. 2. FIG. 3 shows internal details of this device. The upper concentrator housing 4 encloses a concentrating chamber 20.

The floor of the concentrating chamber 20 is filter 24, the upper surface of which supports desiccated concentrating gel beads 26.

The desiccated concentrating gel beads 26 can be insoluble beads or disks that will absorb a substantial volume of water and not introduce any undesirable contaminant into the plasma. They can be dextranomer or acrylamide hydrogel beads that are commercially available (Debrisan from Pharmacia and BIO-GEL P™ from Bio-Rad Laboratories, respectively). Alternatively, other concentrators can be used, such as SEPHADEX™ moisture or water absorbents (available from Pharmacia), silica gel, zeolites, cross-linked agarose, etc., in the form of insoluble inert beads. The beads are used in their desiccated state.

Gel bead agitator 12 is positioned with its bottom edge 28 resting on the top surface of filter base 24. Agitator stem 10 extends upward through a cylindrical stop sleeve 30 in the housing top 8. The stop sleeve 30 extends downward into the concentrating chamber 20 and service to support the agitator stem in a vertical orientation. The bottom edge surface 31 of the stop sleeve 30 constitutes a lower abutment surface. Integral projections 32 extend radially outward from the stirrer agitator stem 10 to a diameter larger than the inner diameter of the stop sleeve 30. The upper surfaces 33 of the projections 32 constitute upper abutment surfaces. As will be described in greater detail hereinafter, the gel bead agitator is rotated about its vertical axis and moved upward and downward in a reciprocal movement to stir the gel beads 26 during the water removal step. The contact of the low abutment edge 31 with the upper abutment surface 33 limits upward movement of the agitator blades or paddles 34 when they are raised during this reciprocal vertical movement of the stem 10.

Figure 5:
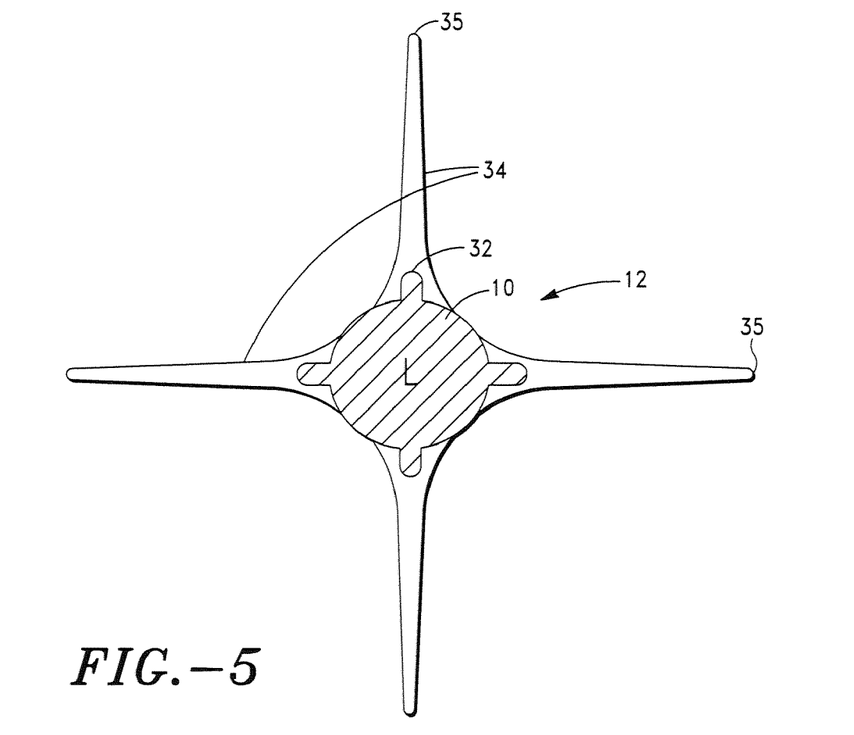
FIG. 5 is cross-sectional view of the agitator component show in FIG. 4, taken along the line 5-5.

Referring to FIGS. 3-5, the agitator comprises a plurality of paddles blades 34 extending radially outwardly from the central chamber stem 41. The outer vertical edge of the agitator blades are sized to make a sliding engagement with the inner surface 38 of the chamber housing 4 (FIG. 3). The distance between the outer edge of the paddles 34 and the inner surface 38 of the chamber housing should be smaller than the diameter of the individual gel beads to prevent individual gel beads from wedging between the agitator and the wall surface. Rotation of stem 10 about its central axis rotates the paddles 34 and stirs the beads 26.

FIG. 4 is a front view of the agitator component of the plasma concentrating device of this invention, and FIG. 5 is a cross-sectional view of the agitator component show in FIG. 4, taken along the line 5-5.

The upper end of the stem 10 can optionally have a plurality of splines 39 that can mate with an optional agitator handle (not shown) or that can function as friction surfaces, facilitating manual rotation of the stem.

Referring to FIG. 3, the lower concentrate chamber housing 6 encloses a concentrate chamber 40 with a sloped bottom 41 leading to a sump or depression 42. The concentrate conduit 18 has a conduit end 44 that extends into the depression 42 to draw in most of the liquid concentrate (not shown) through the concentrate outlet 16 when the pressure in the conduit 18 is reduced.

Figure 6:
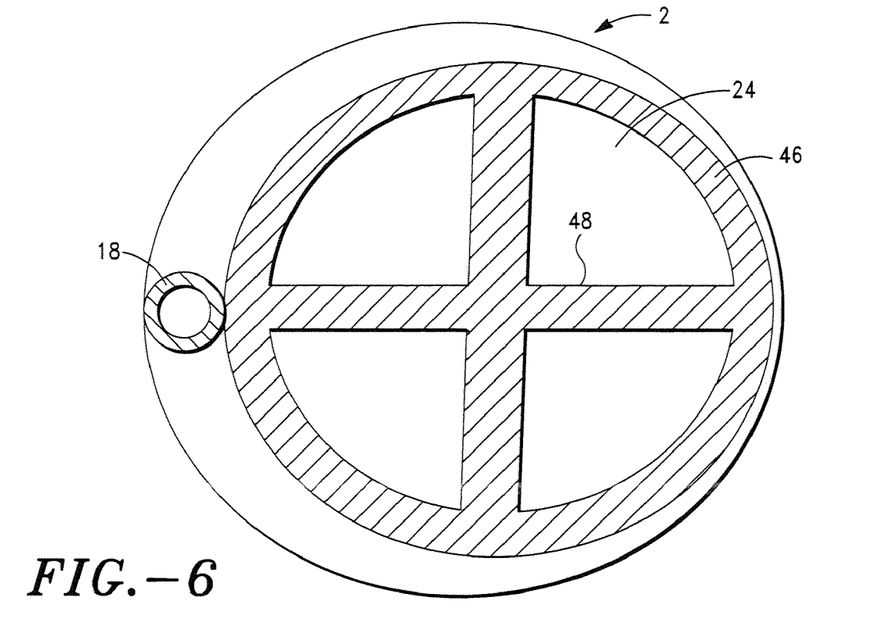
FIG. 6 is a cross-sectional drawing of the plasma concentrating device shown in FIG. 3, taken along the line 6-6.

The construction and function of the filter 24 is described in greater detail with respect to FIG. 6. FIG. 6 is a cross-sectional drawing of the plasma concentrating device shown in FIG. 3, taken along the line 6-6.

The filter 24 is supported by a flat circular ring 46 and flat radial spokes 48. The openings in the support are designed to permit liquid flow through the filter under the pressure of centrifugal force. The filter must retain the plasma above the filter under ambient gravity during the water removal phase and permit plasma concentrate flow therethrough at centrifugal pressures used in the separation. Therefore the filter should retain fluid for at least up to 10 g's and permit flow at the separation gravity. The separation gravity is created when the system is spun in a centrifuge, the centrifugal force being directed in the axial direction through the filter. The higher the centrifugal force applied is during the plasma concentrate separation, the more effective the recovery of the plasma concentrate.

The concentration process has as its critical objective, the removal of water from the plasma without significantly denaturing the fibrinogen component of the plasma. This component provides effective the clotting action of blood and provides the sealing, adhesive and homeostatic properties of the concentrate.

Figure 7:
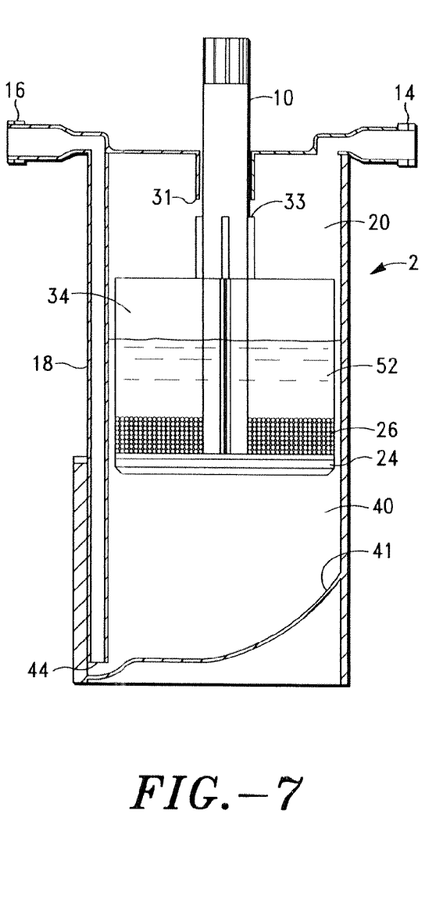
FIG. 7 is a cross-sectional drawing of the plasma concentrating device shown in FIG. 3 after plasma has been introduced into the device.
Figure 8:
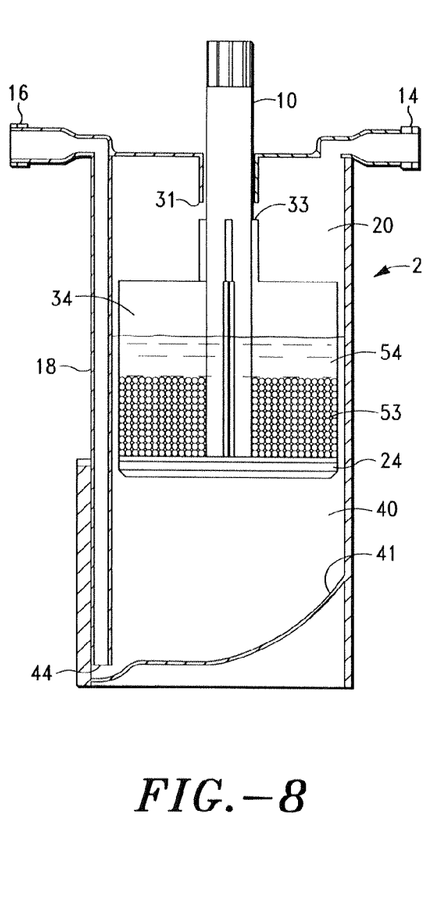
FIG. 8 is a cross-sectional drawing of the plasma concentrating device shown in FIG. 7 after the gel beads have removed water from the plasma, swelling the beads.
Figure 9:
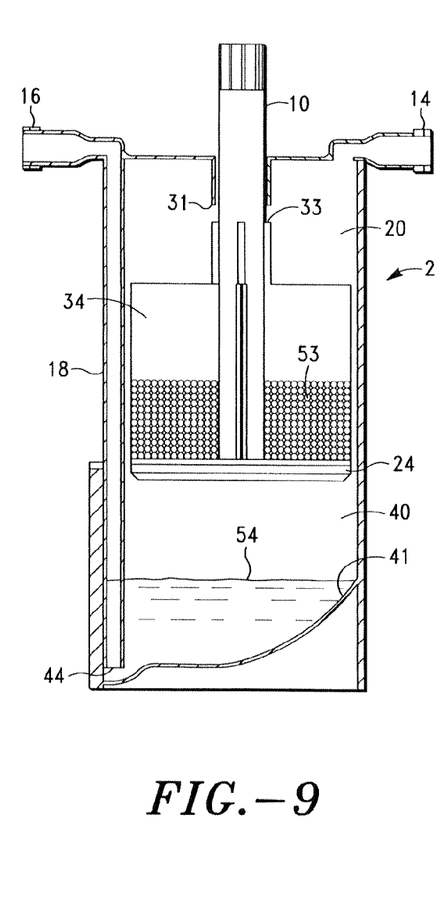
FIG. 9 is a cross-sectional drawing of the plasma concentrating device shown in FIG. 8 after centrifuging, wherein the plasma concentrate has flowed into the plasma concentrate reservoir; and Corresponding reference numerals indicate corresponding parts throughout the several views of the drawings.

The process is illustrated in FIGS. 7-9 wherein FIG. 7 is a cross-sectional drawing of the plasma concentrating device shown in FIG. 3 after plasma has been introduced into the device; FIG. 8 is a cross-sectional drawing of the plasma concentrating device shown in FIG. 7 after the gel beads have removed water from the plasma, swelling the beads; and FIG. 9 is a cross-sectional drawing of the plasma concentrating device shown in FIG. 8 after centrifuging, wherein the plasma concentrate has flowed into the plasma concentrate reservoir.

In the first step of the process, blood plasma 52 (preferably cell free) is introduced into the concentrating chamber 20 through the plasma inlet port 14. The plasma 52 entering the chamber 20 flows to the bottom of the chamber where it contacts the gel beads 26 as shown in FIG. 7.

As the gel beads 26 remove water from the plasma, the plasma contacting each bead's surface thickens, creating gel polarization that it impedes water absorption by the bead. Furthermore, as the thickened plasma becomes more viscous, the beads tend to clump. To disrupt the thickened plasma layer forming on each bead, the agitator stem 10 is rotated around its central axis, moving the agitator blades 34 through the beads and stirring the beads. To break up bead clumps, the agitator blades 34 can be raised and lowered by reciprocal motion of the agitator stem 10 along its central axis, the bottom edges 28 of the blades (FIG. 3) impact the bead clumps against the filter surface disrupting the clumps. The vertical movement of the agitator blades is limited to a range established by the upper surface of the filter 24 range of movement is defined by the floor 4 of the chamber and impingement contact between the abutments 31 and 33. The water swollen beads 53 and the concentrated plasma 54 are shown in FIG. 8. During this concentration stage, the plasma and its components can be concentrated to a concentration of from 1.5-3 times or higher than its original concentration.

The device of this invention is then placed in the cup receptors of a conventional laboratory centrifuge (not shown) and spun at a speed that will create a separation gravity, that is, a centrifugal force that will remove plasmas concentrate from the surface of the gel beads, and cause the plasma concentrate to flow through the filter. The filter can be constructed to allow flow of liquid therethrough at pressures above 10 g's. The centrifugal pressure forces of the plasma concentrate to flow from the bead surface through the filter 24 and into the plasma concentrate reservoir 40. The higher the centrifugal force applied, the more effective will be the stripping of the plasma concentrate from the surface of the gel beads. After centrifugation is completed, the device is removed from the centrifuge.

FIG. 9 shows the device with the plasma concentrate in the reservoir. The plasma concentrate is then drawn from the plasma concentrate reservoir through conduit to the plasma concentrate outlet.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method for concentrating plasma by removing water without significantly denaturing the fibrinogen in the plasma, comprising:
   positioning a plurality of concentrator gel beads in a concentrator chamber of the plasma concentrator;
   positioning a sample volume of plasma in the concentrator chamber of the plasma concentrator;
   moving an actuator stem having a lower agitator end to agitate the sample volume of plasma and the concentrator gel beads in the concentrator chamber with agitator blades extending outwardly from the lower agitator end being positioned in the concentrator chamber;
   concentrating the plasma by removing at least a portion of water from the sample volume of plasma to the concentrator gel beads to form a concentrated plasma volume; and
   removing the concentrated plasma volume through a filter in a lower opening of the concentrator chamber;
   wherein the concentrator chamber includes a top with an upper opening through which an upper end of the actuator stem extends.

2. The method of claim 1, wherein moving the agitator stem at least one of rotating the agitator about its central axis and reciprocally moving the agitator stem about its central axis.

3. The method of claim 1, further comprising agitating the sample volume of plasma and the concentrator gel beads including moving the total volume of the sample volume of plasma and the concentrator gel beads at least by moving the agitator blades near a cylindrical inner wall of the concentrator chamber and the agitator blades have an outer edge in close proximity to the inner wall with a space between the outer edge and the inner wall being less than a diameter of the gel beads.

4. The method of claim 1, further comprising:
   limiting or eliminating upward axial movement by contacting a stop sleeve extending from a top of the concentrator into the concentrator chamber with stop projections of the agitator stem,
   wherein the stop sleeve has a lower abutment surface and the stop projections extend outward beyond the diameter of the stop sleeve, an upper surface of the stop projections positioned to stop upward axial movement of the agitator when contacting a lower abutment surface of the stop sleeve.

5. The method of claim 4, further comprising:
   limiting or eliminating downward movement of the agitator by contacting an upper surface of the filter with a lower surface of the agitator blades; and
   sweeping the upper surface of the filter by contacting the upper surface of the filter with the lower surface of the agitator blades;
   wherein the downward motion of the blades during the reciprocal movement of the agitator being arrested by abutment with the upper surface of the filter.

6. The method of claim 1, further comprising:
   blocking effective flow of plasma through the filter under ambient gravity conditions, but permitting free plasma concentrate flow therethrough under centrifugal forces at the separation gravity.

7. The method of claim 6, wherein the separation gravity is greater than 10 g's.

8. The method of claim 1, further comprising:
   removing the plasma concentrate from the plasma concentrator through a plasma concentrate outlet conduit from a plasma concentrate reservoir;
   wherein removing the plasma concentrate from the plasma concentrate reservoir includes moving the plasma concentrate from a sump formed in a floor of the plasma concentrate reservoir.

9. The method of claim 8, further comprising:
   wherein introducing plasma includes introducing up to 50 mL of plasma into concentration chamber.

10. The method of claim 8, wherein removing water from the plasma includes forming a plasma concentrate having a protein concentration 1.5 to 3 times greater than the protein concentration of the untreated plasma.

11. A method for concentrating plasma by removing water without significantly denaturing the fibrinogen in the plasma, comprising:
   a) introducing the plasma into a concentration chamber containing a plurality of dehydrated concentrator gel beads and an agitator;
   b) removing water from the plasma until the plasma has a protein concentration greater than the protein concentration of the untreated plasma while:
      i) rotating the agitator to stir the beads while they are absorbing water from the plasma to reduce plasma polarization, and
      ii) moving the agitator to break up clumps of beads that form during the stirring; and
   c) applying centrifugal force to the concentrated plasma in an amount sufficient to separate a substantial portion of the plasma concentrate from the beads.

12. The method of claim 11, wherein the agitator having has agitator blades extending outwardly from its lower end, wherein the agitator is supported for rotation about its central axis and for reciprocal movement along its central axis.

13. The method of claim 12, wherein the agitator blades rest on the upper surface of a filter, the agitator blades have a lower portion that sweeps the upper surface of the filter during rotation, and impacts the upper surface of the filter during reciprocal motion of the agitator along its central axis, wherein the agitator is rotated to sweep the upper surface of the filter and stirring beads resting thereupon to reduce plasma polarization, and the agitator is moved in a reciprocal motion to impact the upper surface of the filter and bead clumps forming on the surface during the stirring.

14. The method of claim 13, wherein the filter has a pore that blocks effective flow of plasma therethrough under ambient gravity conditions and permits plasma and plasma concentrate flow therethrough under forces of the centrifugal force.

15. The method of claim 12, wherein rotating the agitator and the agitator blades is performed by engaging a central agitator post from which the agitator blades extend;
   wherein the central agitator post extends out of the concentration chamber.

16. A method for concentrating plasma by removing water without significantly denaturing the fibrinogen in the plasma, comprising:

a) introducing the plasma into a concentration chamber containing a plurality of dehydrated concentrator gel beads and an agitator;
b) removing water from the plasma until the plasma has a protein concentration greater than the protein concentration of the untreated plasma while:
   i) moving the agitator to cause agitation of the beads while they are absorbing water from the plasma to reduce plasma polarization, and
   ii) moving the agitator to break up clumps of beads that form during the agitation; and
c) applying centrifugal force to the concentrated plasma in an amount sufficient to separate a substantial portion of the plasma concentrate from the beads; wherein moving the agitator includes rotating the agitator around a central axis of the agitator and reciprocally moving the agitator its along the central axis.

17. The method of claim 16, further comprising:
blocking effective flow of plasma through a filter under ambient gravity conditions, but permitting free plasma concentrate flow therethrough under centrifugal forces at a separation gravity.

18. The method of claim 17, wherein applying the centrifugal force to the concentrated plasma in an amount sufficient to separate a substantial portion of the plasma concentrate from the beads includes:
placing the plasma concentrator in a receptor of a centrifuge;
applying centrifugal forces to the plasma concentrator with the centrifuge;
removing the plasma concentrate from the surface of the gel beads, and
causing the plasma concentrate to flow through the filter.

19. The method of claim 18, wherein applying centrifugal forces to the plasma concentrator includes applying at least 10 g's of force to cause the plasma concentrate to flow through the filter.

20. The method of claim 19, further comprising:
collecting the concentrated plasma in a plasma concentrate reservoir positioned downstream of the flow of the plasma concentrate through the filter, but within the plasma concentrator.

21. The method of claim 20, further comprising:
removing the plasma concentrate from the plasma concentrator through a plasma concentrate outlet conduit extending from a plasma concentrate reservoir and integrated with the plasma concentrator.

22. The method of claim 21, further comprising:
moving the plasma concentrate to a sump formed in a floor of the plasma concentrate reservoir;
wherein the plasma concentrate outlet conduit is in fluid communication with the sump.

23. A method for concentrating plasma by removing water without significantly denaturing the fibrinogen in the plasma, comprising:
a) introducing the plasma into a concentration chamber containing a plurality of dehydrated concentrator gel beads and an agitator;
b) removing water from the plasma until the plasma has a protein concentration greater than the protein concentration of the untreated plasma while:
   i) moving the agitator to cause agitation of the beads while they are absorbing water from the plasma to reduce plasma polarization, and
   ii) moving the agitator to break up clumps of beads that form during the agitation; and
c) applying centrifugal force to the concentrated plasma in an amount sufficient to separate a substantial portion of the plasma concentrate from the beads;
wherein moving the agitator includes moving the total volume of the plasma and the concentrator gel beads at least because the concentration chamber has a cylindrical inner wall and an agitator blade of the agitator has an outer edge in close proximity to the inner wall with a space between the outer edge and the inner wall being less than a diameter of the gel beads.

24. A method for concentrating plasma by removing water without significantly denaturing the fibrinogen in the plasma, comprising:
a) introducing the plasma into a concentration chamber containing a plurality of dehydrated concentrator gel beads and an agitator;
b) removing water from the plasma until the plasma has a protein concentration greater than the protein concentration of the untreated plasma while:
   i) moving the agitator to cause agitation of the beads while they are absorbing water from the plasma to reduce plasma polarization, and
   ii) moving the agitator to break up clumps of beads that form during the agitation; and
c) applying centrifugal force to the concentrated plasma in an amount sufficient to separate a substantial portion of the plasma concentrate from the beads;
(d) limiting upward movement of the agitator by contacting a stop sleeve extending from a top of the plasma concentrator into the concentration chamber with stop projections of an agitator stem of the agitator, wherein the stop sleeve has a lower abutment surface and the stop projections extend outward beyond the diameter of the stop sleeve, an upper surface of the stop projections constituting abutment surfaces positioned to stop upward axial movement of the agitator when contacting a lower abutment surface of the stop sleeve;
(e) limiting downward movement of the agitator by contacting an upper surface of a filter with a lower surface of agitator blades of the agitator; and
(f) sweeping the upper surface of the filter by contacting the upper surface of the filter with the lower surface of the agitator blades;
wherein the downward motion of the agitator blades during the reciprocal movement of the agitator is arrested by abutment with the upper surface of the filter.

\* \* \* \* \*